US012761143B2

(12) United States Patent
Yang et al.

(10) Patent No.: US 12,761,143 B2
(45) Date of Patent: Oct. 13, 2026

(54) REAL-TIME RADIOMETRIC CORRECTION METHOD AND APPARATUS FOR SPECTRAL REFLECTANCE

(71) Applicant: Information Technology Research Center, Beijing Academy of Agriculture and Forestry Sciences, Beijing (CN)

(72) Inventors: Hao Yang, Beijing (CN); Guijun Yang, Beijing (CN); Bo Xu, Beijing (CN); Xiaodong Yang, Beijing (CN); Haikuan Feng, Beijing (CN); Huiling Long, Beijing (CN); Yang Meng, Beijing (CN); Haitang Hu, Beijing (CN)

(73) Assignee: Information Technology Research Center, Beijing Academy of Agriculture and Forestry Sciences, Beijing (CN)

( * ) Notice: Subject to any disclaimer, the term of this patent is extended or adjusted under 35 U.S.C. 154(b) by 0 days.

(21) Appl. No.: 19/179,001

(22) Filed: Apr. 15, 2025

(65) Prior Publication Data

US 2026/0160677 A1 Jun. 11, 2026

(30) Foreign Application Priority Data

Jun. 27, 2024 (CN) ......................... 202410845774.8

(51) Int. Cl.
*G01N 21/31* (2006.01)
*G01N 21/00* (2006.01)
*G01N 33/00* (2006.01)

(52) U.S. Cl.
CPC ....... *G01N 21/314* (2013.01); *G01N 33/0098* (2013.01); *G01N 2021/3155* (2013.01); *G01N 2201/121* (2013.01)

(58) Field of Classification Search
CPC .... G01N 21/314; G01N 21/35; G01N 21/255; G01N 33/0098; G01N 2021/8466;
(Continued)

(56) References Cited

U.S. PATENT DOCUMENTS 4,779,980 A * 10/1988 Hulstrom .................. G01J 1/42 356/218
10,386,296 B1 * 8/2019 Wolf ...................... G01N 21/35
(Continued)

OTHER PUBLICATIONS

Atsusgi "Plant Sensor Device and Active Optical Measurement Method of Plant", Nov. 30, 2023, WO2023228894 A1 (Year: 2023).*
(Continued)

*Primary Examiner* — Sang H Nguyen
(74) *Attorney, Agent, or Firm* — Bayramoglu Law Offices LLC

(57) ABSTRACT

A real-time radiometric correction method and an apparatus for spectral reflectance are provided. The method includes: obtaining photosynthetically active irradiance measured by a photosynthetically active radiation sensor, where the photosynthetically active radiation sensor includes a cosine corrector; obtaining photosynthetically active irradiance of a target band based on a proportional relationship between the photosynthetically active irradiance and downwelling solar irradiance within a same wavelength range, where the target band is any band in a spectral band obtained by an imaging hyperspectral sensor, and an imaging time point of the imaging hyperspectral sensor is synchronized with a measurement time point of the photosynthetically active radiation sensor; and performing weighted adjustment on the photosynthetically active irradiance of the target band to obtain corrected target irradiance of the target band.

16 Claims, 4 Drawing Sheets

(58) Field of Classification Search
CPC ... G01N 2021/3129; G01N 2021/1797; G01N 2201/1211
See application file for complete search history.

(56) References Cited

U.S. PATENT DOCUMENTS

| | | | | |
|---|---|---|---|---|
| 2011/0273704 | A1* | 11/2011 | Burba | G01J 1/4228 250/237 R |
| 2016/0088802 | A1* | 3/2016 | Nicole | A01G 22/05 315/297 |
| 2019/0377946 | A1* | 12/2019 | Genty | G06N 3/045 |
| 2020/0200683 | A1* | 6/2020 | Aronov | G06T 7/0012 |
| 2021/0365683 | A1* | 11/2021 | Badhwar | G06V 10/763 |
| 2022/0240494 | A1* | 8/2022 | Schonherr | A01B 51/023 |
| 2023/0075132 | A1* | 3/2023 | Lawrence | A01G 13/33 |
| 2024/0033940 | A1* | 2/2024 | Schonherr | A01G 7/06 |

OTHER PUBLICATIONS

Floran et al "Optomechanical System for Light Regulation and Electricity Production", Sep. 7, 2023, WO 2023165728 A1 (Year: 2023).*
Atsushi "Optical Vegetation Index Sensor", Jul. 7, 2011, JP 2011133451 A (Year: 2011).*

* cited by examiner

REAL-TIME RADIOMETRIC CORRECTION METHOD AND APPARATUS FOR SPECTRAL REFLECTANCE

CROSS REFERENCE TO THE RELATED APPLICATIONS

This application is based upon and claims priority to Chinese Patent Application No. 202410845774.8, filed on Jun. 27, 2024, the entire contents of which are incorporated herein by reference.

TECHNICAL FIELD

The present disclosure relates to the technical field of radiometric correction, and specifically, to a real-time radiometric correction method and apparatus for spectral reflectance.

BACKGROUND

High-precision spectral reflectance of a target ground object is a foundation of spectral quantitative inversion and even optical remote sensing. The high-precision spectral reflectance of the target ground object is a prerequisite for many high-precision quantitative remote sensing applications, such as time series change analysis of crops. Only high-precision reflectance of a single remote sensing observation can ensure comparability of observation results at different time points in a long-term time-series observation. Therefore, obtaining the high-precision spectral reflectance is helpful for applying a fine quantitative scenario and discovering more remote sensing patterns, which is of great significance.

Spectral reflectance of the target ground object is usually calculated based on irradiance of sunlight incident on the target ground object. However, currently, some irradiance measurement methods are only suitable completely stable weather and light conditions, some irradiance measurement methods have insufficient measurement accuracy and are only suitable for multispectral sensors, and some irradiance measurement methods require high-cost instruments. All these methods are difficult to apply to changeable and complex scenarios of spectral remote sensing.

SUMMARY

Embodiments of the present disclosure provide a real-time radiometric correction method and apparatus for spectral reflectance, which are used to solve the technical problems that currently, some irradiance measurement methods are only suitable for completely stable weather and light conditions, some irradiance measurement methods have insufficient measurement accuracy and are only suitable for multispectral sensors, some irradiance measurement methods require high-cost instruments, and all these methods are difficult to apply to changeable and complex scenarios of spectral remote sensing.

According to a first aspect, an embodiment of the present disclosure provides a real-time radiometric correction method for spectral reflectance, including:

- obtaining photosynthetically active irradiance measured by a photosynthetically active radiation sensor, where the photosynthetically active radiation sensor includes a cosine corrector;
- obtaining photosynthetically active irradiance of a target band based on a proportional relationship between the photosynthetically active irradiance and downwelling solar irradiance within a same wavelength range, where the downwelling solar irradiance is obtained based on a standard solar spectral irradiance model, the target band is any band in a spectral band obtained by an imaging hyperspectral sensor, and an imaging time point of the imaging hyperspectral sensor is synchronized with a measurement time point of the photosynthetically active radiation sensor; and
- performing weighted adjustment on the photosynthetically active irradiance of the target band to obtain corrected target irradiance of the target band.

In an embodiment, the obtaining photosynthetically active irradiance of a target band based on a proportional relationship between the photosynthetically active irradiance and downwelling solar irradiance within a same wavelength range includes:

- calculating a first total value of the photosynthetically active irradiance and a second total value of the downwelling solar irradiance within the same wavelength range;
- calculating a ratio of the first total value to the second total value; and
- calculating a product of the ratio and downwelling solar irradiance of the target band to obtain the photosynthetically active irradiance of the target band.

In an embodiment, the performing weighted adjustment on the photosynthetically active irradiance of the target band to obtain corrected target irradiance of the target band includes:

- within a wavelength range of the imaging hyperspectral sensor, performing the weighted adjustment on the photosynthetically active irradiance of the target band by using a spectral response function of the imaging hyperspectral sensor, to obtain the corrected target irradiance of the target band.

In an embodiment, after obtaining the corrected target irradiance of the target band, the real-time radiometric correction method includes:

- calibrating radiance of the imaging hyperspectral sensor in the target band to obtain target radiance of the target band; and
- obtaining spectral reflectance of the target band based on the target irradiance and the target radiance.

In an embodiment, the calibrating radiance of the imaging hyperspectral sensor in the target band to obtain target radiance of the target band includes:

- calibrating the radiance based on a digital number and a radiometric calibration coefficient of the imaging hyperspectral sensor in the target band to obtain the target radiance of the target band.

In an embodiment, the obtaining spectral reflectance of the target band based on the target irradiance and the target radiance includes:

- obtaining the spectral reflectance of the target band based on a ratio of the target radiance to the target irradiance.

According to a second aspect, an embodiment of the present disclosure provides a real-time radiometric correction apparatus for spectral reflectance, including:

- a photosynthetically active irradiance obtaining module configured to obtain photosynthetically active irradiance measured by a photosynthetically active radiation sensor, where the photosynthetically active radiation sensor includes a cosine corrector;
- a photosynthetically active irradiance calculation module configured to obtain photosynthetically active irradiance of a target band based on a proportional relationship between the photosynthetically active irradiance and downwelling solar irradiance within a same wavelength range, where the downwelling solar irradiance is obtained based on a standard solar spectral irradiance model, the target band is any band in a spectral band obtained by an imaging hyperspectral sensor, and an imaging time point of the imaging hyperspectral sensor is synchronized with a measurement time point of the photosynthetically active radiation sensor; and a photosynthetically active irradiance adjustment module configured to perform weighted adjustment on the photosynthetically active irradiance of the target band to obtain corrected target irradiance of the target band.

According to a third aspect, an embodiment of the present disclosure provides an electronic device, including a processor and a memory storing a computer program, where the processor executes the computer program to perform the steps of the real-time radiometric correction method for spectral reflectance in the first aspect.

According to a fourth aspect, an embodiment of the present disclosure provides a computer program product, including a computer program, where the computer program is executed by a processor to perform the steps of the real-time radiometric correction method for spectral reflectance in the first aspect.

According to a fifth aspect, an embodiment of the present disclosure provides a non-transitory computer-readable storage medium storing a computer program, where the computer program is executed by a processor to perform the steps of the real-time radiometric correction method for spectral reflectance in the first aspect.

The real-time radiometric correction method and apparatus for spectral reflectance provided in the present disclosure obtain the photosynthetically active irradiance measured by the photosynthetically active radiation sensor, where the photosynthetically active radiation sensor includes the cosine corrector; obtain the photosynthetically active irradiance of the target band based on the proportional relationship between the photosynthetically active irradiance and the downwelling solar irradiance within the same wavelength range, where the downwelling solar irradiance is obtained based on the standard solar spectral irradiance model, the target band is the any band in the spectral band obtained by the imaging hyperspectral sensor, and the imaging time point of the imaging hyperspectral sensor is synchronized with the measurement time point of the photosynthetically active radiation sensor; and perform the weighted adjustment on the photosynthetically active irradiance of the target band to obtain the corrected target irradiance of the target band. The present disclosure performs radiometric correction based on the photosynthetically active irradiance measured by the photosynthetically active radiation sensor. As the photosynthetically active radiation sensor includes the cosine corrector, the photosynthetically active radiation sensor is able to record a sunlight flux with high precision at different solar elevation angles, and is not affected by weather conditions in a measurement process. Therefore, the photosynthetically active radiation sensor can accurately and stably measure the photosynthetically active irradiance under any complex and changeable weather conditions. The photosynthetically active radiation sensor can be applied not only to a multispectral sensor but also to a hyperspectral sensor without a need to install high-cost instruments, achieving low-cost and high-precision real-time acquisition of spectral reflectance of a target ground object under the complex and changeable weather conditions. This makes the present disclosure applicable to changeable and complex scenarios of spectral remote sensing.

BRIEF DESCRIPTION OF THE DRAWINGS

To describe the technical solutions in the embodiments of the present disclosure or in the prior art more clearly, the following briefly describes the accompanying drawings required for describing the embodiments or the prior art. Apparently, the accompanying drawings in the following description show some embodiments of the present disclosure, and a person of ordinary skill in the art may still derive other accompanying drawings from these accompanying drawings without creative efforts.

DETAILED DESCRIPTION OF THE EMBODIMENTS

Figure 1:
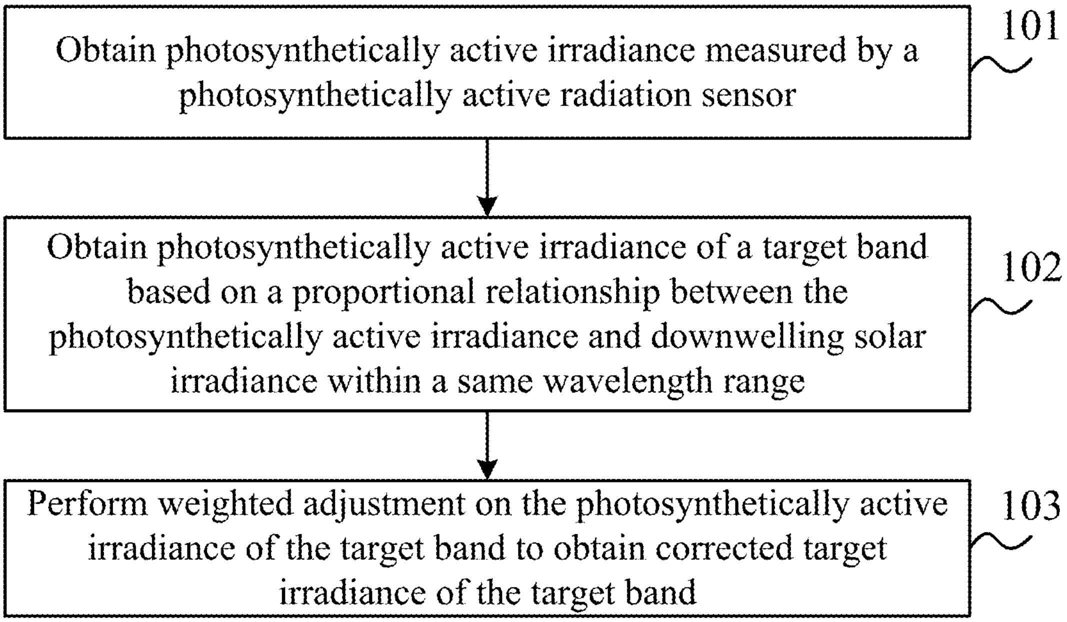
FIG. 1 is a first schematic flowchart of a real-time radiometric correction method for spectral reflectance according to an embodiment of the present disclosure.

In order to make the objectives, technical solutions, and advantages of the present disclosure clearer, the following clearly and completely describes the technical solutions in the present disclosure with reference to the accompanying drawings in the embodiments of the present disclosure. Apparently, the described embodiments are some rather than all of the embodiments of the present disclosure. All other embodiments obtained by those of ordinary skill in the art based on the embodiments of the present disclosure without creative efforts should fall within the protection scope of the present disclosure.

It should be noted that in the description of the embodiments of the present disclosure, terms “including”, “comprising”, “containing”, or any other variants thereof are intended to cover non-exclusive inclusion, such that a process, a method, an article, or a device that includes a series of elements includes not only those elements but also other elements not explicitly listed, or also includes elements inherent to this process, method, article, or device. Without more restrictions, an element defined by a sentence “including/comprising a . . . ” does not exclude the existence of other identical elements in a process, a method, an article, or a device that includes the element. Orientations or positional relationships indicated by terms such as “upper” and “lower” are based on the orientations or positional relationships shown in the accompanying drawings, which are only for convenience of describing the present disclosure and simplifying the description, rather than indicating or implying that the mentioned apparatus or element must have a particular orientation and be constructed and operated in a particular orientation, and therefore should not be construed as limiting the present disclosure. Unless otherwise clearly specified and limited, terms such as "installation", "interconnection", and "connection" should be understood in a broad sense. For example, the "connection" may be a fixed connection, a detachable connection, or an integral connection; may be a mechanical connection or an electrical connection; may be a direct connection or an indirect connection by means of an intermediate medium; and may be an internal communication between two elements. Those of ordinary skill in the art may understand specific meanings of the above terms in the present disclosure based on specific situations.

The terms such as "first" and "second" in the present disclosure are used to distinguish between similar objects and are not intended to describe a specific order or sequence. It should be understood that data used in such a way may be interchanged under appropriate circumstances, such that the embodiments of the present disclosure can be implemented in an order other than those illustrated or described herein, the objects distinguished by "first", "second", and the like are usually of one type, and a quantity of objects is not limited. For example, one or more first objects may be provided. In addition, "and/or" means at least one of the connected objects, and the character "/" generally indicates an "or" relationship between associated objects.

FIG. 1 is a first schematic flowchart of a real-time radiometric correction method for spectral reflectance according to an embodiment of the present disclosure. Referring to FIG. 1, the real-time radiometric correction method for spectral reflectance provided in this embodiment of the present disclosure may include the following steps:

101: Obtain photosynthetically active irradiance measured by a photosynthetically active radiation sensor.

The photosynthetically active radiation sensor includes a cosine corrector.

102: Obtain photosynthetically active irradiance of a target band based on a proportional relationship between the photosynthetically active irradiance and downwelling solar irradiance within a same wavelength range.

The downwelling solar irradiance is obtained based on a standard solar spectral irradiance model, the target band is any band in a spectral band obtained by an imaging hyperspectral sensor, and an imaging time point of the imaging hyperspectral sensor is synchronized with a measurement time point of the photosynthetically active radiation sensor.

103: Perform weighted adjustment on the photosynthetically active irradiance of the target band to obtain corrected target irradiance of the target band.

In the step 101, the photosynthetically active radiation sensor can measure and record sunlight energy with a wavelength range of 400 nm to 700 nm. In this embodiment, a LI-COR 190R photosynthetically active radiation sensor may be used, and a cosine corrector in the photosynthetically active radiation sensor has excellent cosine correction performance.

In the step 102, the downwelling solar irradiance is generally irradiance of sunlight in a wavelength range of 400 nm to 1000 nm at a top of atmosphere, and the wavelength range exceeds a wavelength range of the photosynthetically active irradiance. Therefore, the same wavelength range may be set to 400 nm to 700 nm. Based on a proportional relationship between photosynthetically active irradiance and downwelling solar irradiance within the wavelength range of 400 nm to 700 nm, the photosynthetically active irradiance of the target band can be obtained.

The photosynthetically active radiation sensor and the imaging hyperspectral sensor may be integrated on an integrated circuit board. The integrated circuit board synchronously controls the photosynthetically active radiation sensor and the imaging hyperspectral sensor, so as to control their exposure time and data recording. It should be noted that the imaging time point of the imaging hyperspectral sensor is synchronized with the measurement time point of the photosynthetically active radiation sensor, which does not require an exact one-to-one correspondence between the imaging time point of the imaging hyperspectral sensor and the measurement time point of the photosynthetically active radiation sensor, and only requires that the imaging time point is a part of the measurement time point or the measurement time is a part of the imaging time point within a same time period. For example, the imaging hyperspectral sensor has two imaging time points T1 and T2 within one second, and the photosynthetically active radiation sensor has two measurement time points within the same one second. If the measurement time points are also T1 and T2, the imaging time points are completely synchronized the measurement time points. If the measurement moments are T1, T2, T3, T4, and T5, since the imaging time points are included in the measurement time points and are a part of the measurement time points, it can also be considered that the imaging time points of the imaging hyperspectral sensor are synchronized with the measurement time points of the photosynthetically active radiation sensor.

For some types of imaging hyperspectral sensors, their internal hyperspectral cameras have different imaging time points in different bands. Therefore, a measurement frequency of the photosynthetically active radiation sensor may be set to be higher than an imaging frequency of the imaging hyperspectral sensor to ensure that all imaging time points in a plurality of bands can be synchronized with the measurement time point of the photosynthetically active radiation sensor.

Further, since the imaging time point of the imaging hyperspectral sensor is synchronized with the measurement time point of the photosynthetically active radiation sensor, and the target band is the any band in the spectral band obtained by the imaging hyperspectral sensor, the obtained corrected target irradiance of the target band can accurately characterize irradiance of the corresponding band in spectral imaging of the imaging hyperspectral sensor. Therefore, spectral reflectance of a corresponding target ground object in the spectral imaging can be accurately calculated based on the irradiance.

Figure 6:
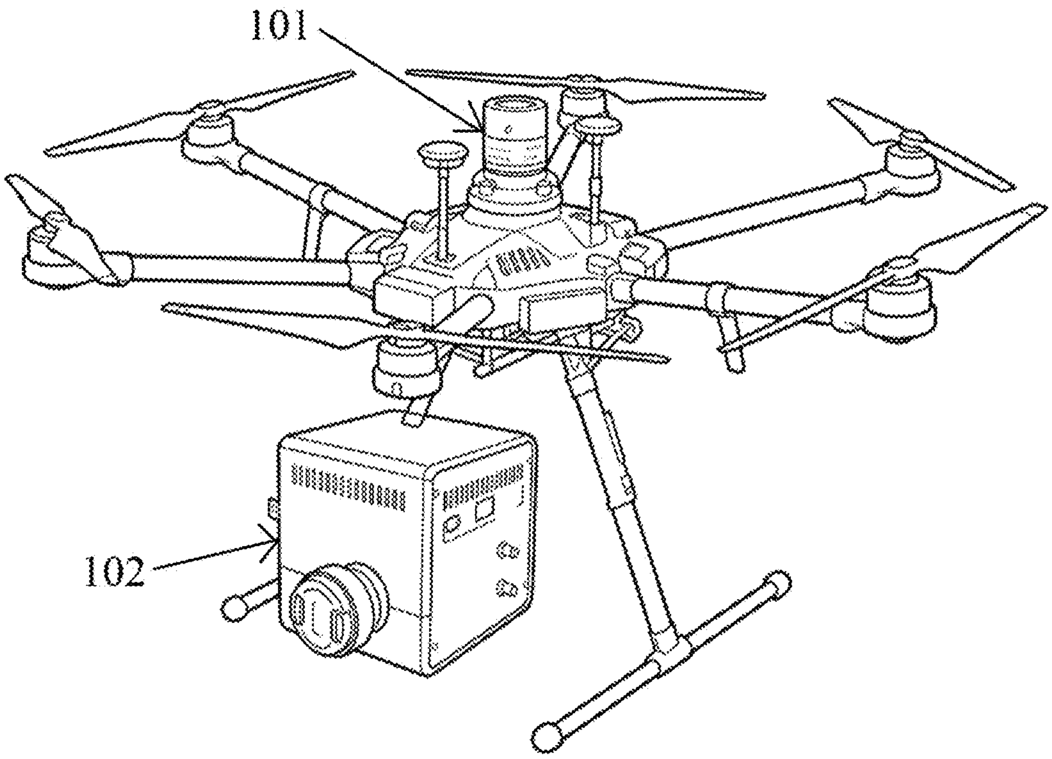
FIG. 6 shows a photosynthetically active radiation sensor 101 and an imaging hyperspectral sensor 102 which can be applied to an unmanned aerial vehicle.

It should be noted that the photosynthetically active radiation sensor, the imaging hyperspectral sensor, and the integrated circuit board may be applied to an unmanned aerial vehicle, or may be applied to various ground carriers such as a portable ground carrier, a tower base, and a vehicle. FIG. 6 shows a photosynthetically active radiation sensor 101 and an imaging hyperspectral sensor 102 which can be applied to an unmanned aerial vehicle.

The real-time radiometric correction method for spectral reflectance provided in this embodiment obtains the photosynthetically active irradiance measured by the photosynthetically active radiation sensor, where the photosynthetically active radiation sensor includes the cosine corrector; obtains the photosynthetically active irradiance of the target band based on the proportional relationship between the photosynthetically active irradiance and the downwelling solar irradiance within the same wavelength range, where the downwelling solar irradiance is obtained based on the standard solar spectral irradiance model, the target band is the any band in the spectral band obtained by the imaging hyperspectral sensor, and the imaging time point of the imaging hyperspectral sensor is synchronized with the measurement time point of the photosynthetically active radiation sensor; and performs the weighted adjustment on the photosynthetically active irradiance of the target band to obtain the corrected target irradiance of the target band. This embodiment performs radiometric correction based on the photosynthetically active irradiance measured by the photosynthetically active radiation sensor. As the photosynthetically active radiation sensor includes the cosine corrector, the photosynthetically active radiation sensor is able to record a sunlight flux with high precision at different solar elevation angles, and is not affected by weather conditions in a measurement process. Therefore, the photosynthetically active radiation sensor can accurately and stably measure the photosynthetically active irradiance under any complex and changeable weather conditions. The photosynthetically active radiation sensor can be applied not only to a multispectral sensor but also to a hyperspectral sensor without a need to install high-cost instruments, achieving low-cost and high-precision real-time acquisition of spectral reflectance of a target ground object under the complex and changeable weather conditions. This makes this embodiment applicable to changeable and complex scenarios of spectral remote sensing.

Figure 2:
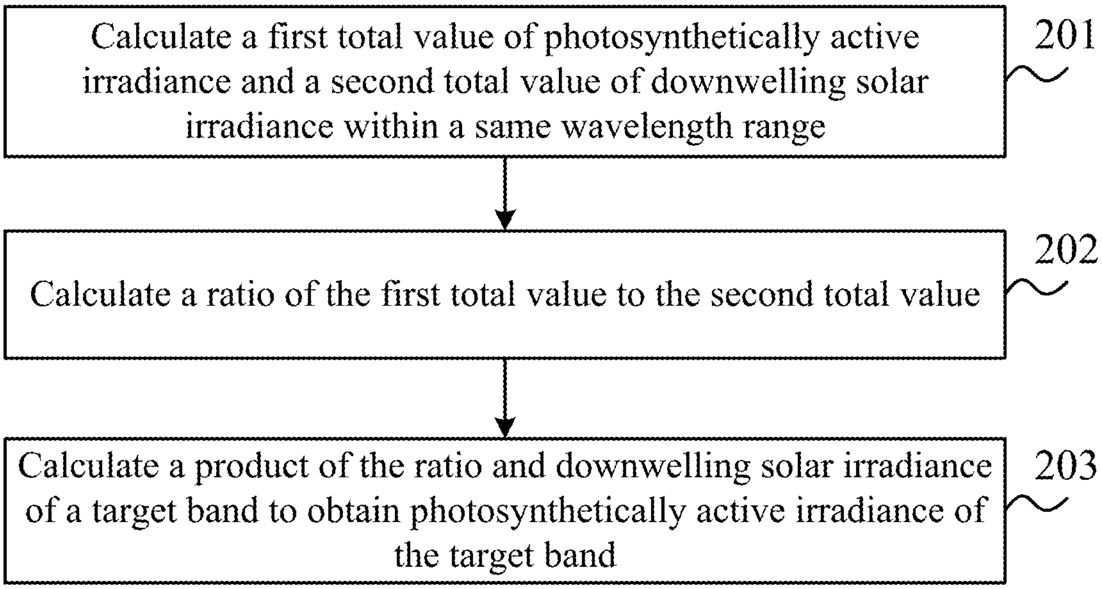
FIG. 2 is a second schematic flowchart of a real-time radiometric correction method for spectral reflectance according to an embodiment of the present disclosure.

FIG. 2 is a second schematic flowchart of the real-time radiometric correction method for spectral reflectance according to this embodiment of the present disclosure. Referring to FIG. 2, in an embodiment, the obtaining photosynthetically active irradiance of a target band based on a proportional relationship between the photosynthetically active irradiance and downwelling solar irradiance within a same wavelength range can include the following steps:

201: Calculate a first total value of the photosynthetically active irradiance and a second total value of the downwelling solar irradiance within the same wavelength range.

202: Calculate a ratio of the first total value to the second total value.

203: Calculate a product of the ratio and downwelling solar irradiance of the target band to obtain the photosynthetically active irradiance of the target band.

In the step 201, a first total value of the photosynthetically active irradiance and a second total value of the downwelling solar irradiance within the wavelength range of 400 nm to 700 nm are calculated.

Both the first total value and the second total value are obtained by adding up irradiance corresponding to a wavelength selected at intervals of 1 nm.

Further, after the photosynthetically active irradiance of the target band is obtained, within a wavelength range of the imaging hyperspectral sensor, the weighted adjustment can also be performed on the photosynthetically active irradiance of the target band by using a spectral response function of the imaging hyperspectral sensor, to obtain the corrected target irradiance of the target band.

In this embodiment, photosynthetically active irradiance is a spectral wavelength range mainly used by plants for photosynthesis. The photosynthetically active irradiance of the target band is obtained based on a stable proportional relationship between the photosynthetically active irradiance and standard downwelling solar irradiance. Then, the weighted adjustment is performed on the photosynthetically active irradiance of the target band by using the spectral response function of the imaging hyperspectral sensor. Therefore, the target irradiance is closer to true irradiance of spectral imaging of crops in the imaging hyperspectral sensor, which helps to subsequently obtain accurate spectral reflectance of a target crop based on the irradiance.

Figure 3:
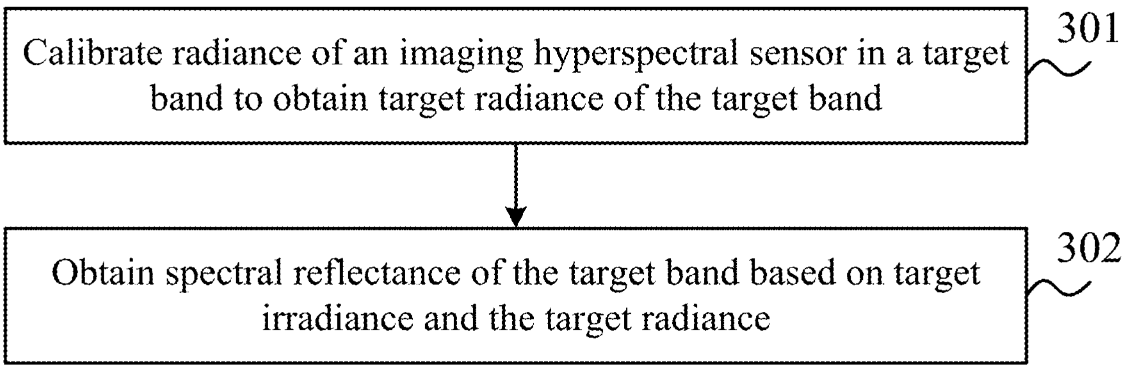
FIG. 3 is a third schematic flowchart of a real-time radiometric correction method for spectral reflectance according to an embodiment of the present disclosure.

FIG. 3 is a third schematic flowchart of the real-time radiometric correction method for spectral reflectance according to this embodiment of the present disclosure. Referring to FIG. 3, in an embodiment, after obtaining the corrected target irradiance of the target band, the real-time radiometric correction method may include the following steps:

301: Calibrate radiance of the imaging hyperspectral sensor in the target band to obtain target radiance of the target band.

302: Obtain spectral reflectance of the target band based on the target irradiance and the target radiance.

In the step 301, the radiance can be calibrated based on a digital number and a radiometric calibration coefficient of the imaging hyperspectral sensor in the target band to obtain the target radiance $L_\lambda$ of the target band $\lambda$. A specific formula may be as follows:

$$L_\lambda = DN_\lambda * \text{Gain}_\lambda + \text{Offset}_\lambda.$$

In the above formula, $DN_\lambda$ represents the digital number in the target band $\lambda$, and $\text{Gain}_\lambda$ and $\text{Offset}_\lambda$ represent radiometric calibration coefficients in the target band $\lambda$.

In the step 302, the spectral reflectance $R_\lambda$ of the target band $\lambda$ can be obtained based on a ratio of the target radiance to the target irradiance. A specific formula may be as follows:

$$R_\lambda = \pi * L_\lambda / E_\lambda.$$

In the above formula, $E_\lambda$ represents the target irradiance.

In a current spectral reflectance calculation method, due to a limitation on irradiance measurement, it is impossible to obtain high-precision spectral reflectance of the target ground object in real time. Even if a plurality of spectral images obtained by the imaging hyperspectral sensor on a single unmanned aerial vehicle are concatenated, due to different accuracy of spectral reflectance, a yin-yang symbol is generated in a concatenated image, and quantitative remote sensing cannot be applied.

This implementation calibrates the radiance of the target band to convert the digital number recorded by the imaging hyperspectral sensor into an actual physical quantity, namely the radiance. Based on the radiance and the accurately measured irradiance, high-precision spectral reflectance of the target band in the spectral imaging of the imaging hyperspectral sensor can be obtained, in other words, the high-precision spectral reflectance of the corresponding target ground object in the target band in the spectral imaging is obtained. In this way, the spectral image can be used for the quantitative remote sensing.

The following describes a real-time radiometric correction apparatus for spectral reflectance provided in the embodiments of the present disclosure. The real-time radiometric correction apparatus for spectral reflectance in the following description and the above real-time radiometric correction method for spectral reflectance can be cross-referenced.

Figure 4:
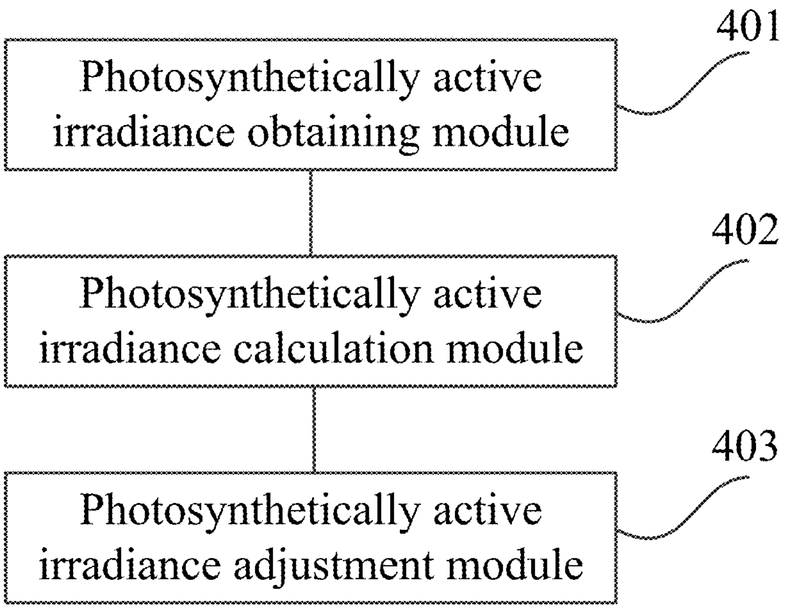
FIG. 4 is a schematic structural diagram of a real-time radiometric correction apparatus for spectral reflectance according to an embodiment of the present disclosure.

FIG. 4 is a schematic structural diagram of a real-time radiometric correction apparatus for spectral reflectance according to an embodiment of the present disclosure. Referring to FIG. 4, the real-time radiometric correction apparatus for spectral reflectance provided in this embodiment of the present disclosure may include:

a photosynthetically active irradiance obtaining module 401 configured to obtain photosynthetically active irradiance measured by a photosynthetically active radiation sensor, where the photosynthetically active radiation sensor includes a cosine corrector;

a photosynthetically active irradiance calculation module 402 configured to obtain photosynthetically active irradiance of a target band based on a proportional relationship between the photosynthetically active irradiance and downwelling solar irradiance within a same wavelength range, where the downwelling solar irradiance is obtained based on a standard solar spectral irradiance model, the target band is any band in a spectral band obtained by an imaging hyperspectral sensor, and an imaging time point of the imaging hyperspectral sensor is synchronized with a measurement time point of the photosynthetically active radiation sensor; and a photosynthetically active irradiance adjustment module 403 configured to perform weighted adjustment on the photosynthetically active irradiance of the target band to obtain corrected target irradiance of the target band.

The real-time radiometric correction apparatus for spectral reflectance provided in this embodiment obtains the photosynthetically active irradiance measured by the photosynthetically active radiation sensor, where the photosynthetically active radiation sensor includes the cosine corrector; obtains the photosynthetically active irradiance of the target band based on the proportional relationship between the photosynthetically active irradiance and the downwelling solar irradiance within the same wavelength range, where the downwelling solar irradiance is obtained based on the standard solar spectral irradiance model, the target band is the any band in the spectral band obtained by the imaging hyperspectral sensor, and the imaging time point of the imaging hyperspectral sensor is synchronized with the measurement time point of the photosynthetically active radiation sensor; and performs the weighted adjustment on the photosynthetically active irradiance of the target band to obtain the corrected target irradiance of the target band. This embodiment performs radiometric correction based on the photosynthetically active irradiance measured by the photosynthetically active radiation sensor. As the photosynthetically active radiation sensor includes the cosine corrector, the photosynthetically active radiation sensor is able to record a sunlight flux with high precision at different solar elevation angles, and is not affected by weather conditions in a measurement process. Therefore, the photosynthetically active radiation sensor can accurately and stably measure the photosynthetically active irradiance under any complex and changeable weather conditions. The photosynthetically active radiation sensor can be applied not only to a multispectral sensor but also to a hyperspectral sensor without a need to install high-cost instruments, achieving low-cost and high-precision real-time acquisition of spectral reflectance of a target ground object under the complex and changeable weather conditions. This makes this embodiment applicable to changeable and complex scenarios of spectral remote sensing.

In an embodiment, the photosynthetically active irradiance calculation module 402 is specifically configured to:

calculate a first total value of the photosynthetically active irradiance and a second total value of the downwelling solar irradiance within the same wavelength range;

calculate a ratio of the first total value to the second total value; and calculate a product of the ratio and downwelling solar irradiance of the target band to obtain the photosynthetically active irradiance of the target band.

In an embodiment, the photosynthetically active irradiance adjustment module 403 is specifically configured to:

within a wavelength range of the imaging hyperspectral sensor, perform the weighted adjustment on the photosynthetically active irradiance of the target band by using a spectral response function of the imaging hyperspectral sensor, to obtain the corrected target irradiance of the target band.

In an embodiment, a spectral reflectance calculation module (not shown in the figure) is further included and configured to:

calibrate radiance of the imaging hyperspectral sensor in the target band to obtain target radiance of the target band; and obtain spectral reflectance of the target band based on the target irradiance and the target radiance.

In an embodiment, the spectral reflectance calculation module is specifically configured to:

calibrate the radiance based on a digital number and a radiometric calibration coefficient of the imaging hyperspectral sensor in the target band to obtain the target radiance of the target band.

In an embodiment, the spectral reflectance calculation module is specifically configured to:

obtain the spectral reflectance of the target band based on a ratio of the target radiance to the target irradiance.

Figure 5:
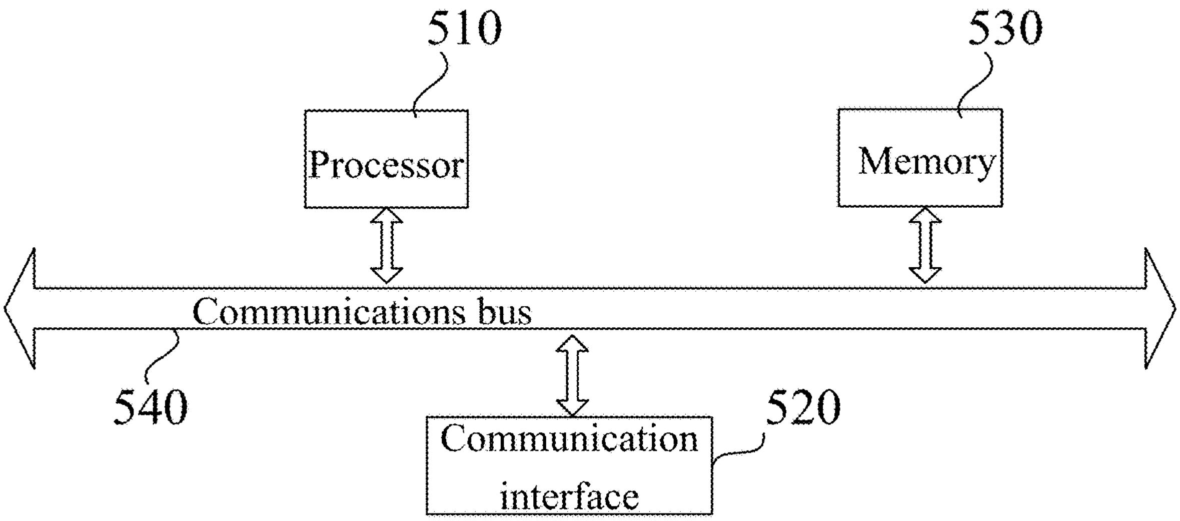
FIG. 5 is a schematic structural diagram of an electronic device according to an embodiment of the present disclosure.

FIG. 5 illustrates a schematic structural diagram of an electronic device. As shown in FIG. 5, the electronic device may include: a processor 510, a communication interface 520, a memory 530, and a communication bus 540. The processor 510, the communication interface 520, and the memory 530 communicate with one another by means of the communication bus 540. The processor 510 can call a computer program in the memory 530 to perform steps of a real-time radiometric correction method for spectral reflectance, for example, including:

obtaining photosynthetically active irradiance measured by a photosynthetically active radiation sensor, where the photosynthetically active radiation sensor includes a cosine corrector;

obtaining photosynthetically active irradiance of a target band based on a proportional relationship between the photosynthetically active irradiance and downwelling solar irradiance within a same wavelength range, where the downwelling solar irradiance is obtained based on a standard solar spectral irradiance model, the target band is any band in a spectral band obtained by an imaging hyperspectral sensor, and an imaging time point of the imaging hyperspectral sensor is synchronized with a measurement time point of the photosynthetically active radiation sensor; and performing weighted adjustment on the photosynthetically active irradiance of the target band to obtain corrected target irradiance of the target band.

Besides, a logic instruction in the memory 530 may be implemented as a software function unit and be stored in a computer-readable storage medium when sold or used as a separate product. Based on such an understanding, the technical solutions in the present disclosure essentially, or the part contributing to the prior art, or some of the technical solutions may be implemented in a form of a software product. The computer software product is stored in a storage medium, and includes several instructions for instructing a computer device (which may be a personal computer, a server, a network device, or the like) to perform all or some of the steps of the method described in the embodiments of the present disclosure. The foregoing storage medium includes any medium that can store program code, such as a universal serial bus (USB) flash disk, a mobile hard disk, a read-only memory (ROM), a random access memory (RAM), a magnetic disk, or an optical disk.

According to another aspect, the embodiments of the present disclosure further provide a computer program product. The computer program product includes a computer program. The computer program may be stored on a non-transitory computer-readable storage medium. When the computer program is executed by a processor, a computer can execute the steps of the real-time radiometric correction method for spectral reflectance in the above embodiments, for example, including:

obtaining photosynthetically active irradiance measured by a photosynthetically active radiation sensor, where the photosynthetically active radiation sensor includes a cosine corrector;

obtaining photosynthetically active irradiance of a target band based on a proportional relationship between the photosynthetically active irradiance and downwelling solar irradiance within a same wavelength range, where the downwelling solar irradiance is obtained based on a standard solar spectral irradiance model, the target band is any band in a spectral band obtained by an imaging hyperspectral sensor, and an imaging time point of the imaging hyperspectral sensor is synchronized with a measurement time point of the photosynthetically active radiation sensor; and performing weighted adjustment on the photosynthetically active irradiance of the target band to obtain corrected target irradiance of the target band.

According to another aspect, the embodiments of the present disclosure further provide a non-transitory computer-readable storage medium, storing a computer program thereon. The computer program is executed by a processor to perform the steps of the real-time radiometric correction method for spectral reflectance in the above embodiments, for example, including:

obtaining photosynthetically active irradiance measured by a photosynthetically active radiation sensor, where the photosynthetically active radiation sensor includes a cosine corrector;

obtaining photosynthetically active irradiance of a target band based on a proportional relationship between the photosynthetically active irradiance and downwelling solar irradiance within a same wavelength range, where the downwelling solar irradiance is obtained based on a standard solar spectral irradiance model, the target band is any band in a spectral band obtained by an imaging hyperspectral sensor, and an imaging time point of the imaging hyperspectral sensor is synchronized with a measurement time point of the photosynthetically active radiation sensor; and performing weighted adjustment on the photosynthetically active irradiance of the target band to obtain corrected target irradiance of the target band.

The non-transitory computer-readable storage medium may be any available medium accessible by a processor, or a data storage device, including but not limited to a magnetic memory (such as a floppy disk, a hard disk, a magnetic tape, and a magneto-optical (MO) disk), an optical memory (such as a CD, a DVD, a BD, and an HVD), and a semiconductor memory (such as a ROM, an EPROM, an EEPROM, a non-volatile memory (NAND FLASH), and a solid state drive (SSD)).

The apparatus embodiment described above is merely schematic. The unit described as a separate component may or may not be physically separated, and a component displayed as a unit may or may not be a physical unit, that is, the component may be located at one place, or distributed on a plurality of network units. Some or all of the modules may be selected based on actual needs to achieve the objectives of the solutions of the embodiments. A person of ordinary skill in the art can understand and implement the embodiments without creative efforts.

Through the description of the foregoing implementations, a person skilled in the art can clearly understand that the implementations may be implemented by means of software plus a necessary universal hardware platform, or certainly, may be implemented by hardware. Based on such an understanding, the foregoing technical solutions essentially or the part contributing to the prior art may be embodied in a form of a software product. The computer software product may be stored in a computer-readable storage medium, such as a ROM/RAM, a magnetic disk, or an optical disk, and includes several instructions for instructing a computer device (which may be a personal computer, a server, or a network device) to execute the method described in the embodiments or some of the embodiments.

Finally, it should be noted that the foregoing embodiments are merely used to explain the technical solutions of the present disclosure, but are not intended to limit the same. Although the present disclosure is described in detail with reference to the foregoing embodiments, those of ordinary skill in the art should understand that they can still modify the technical solutions described in the foregoing embodiments, or make equivalent substitutions on some technical features therein. These modifications or substitutions do not make the essence of the corresponding technical solutions deviate from the spirit and scope of the technical solutions of the embodiments of the present disclosure.

What is claimed is:

1. A real-time radiometric correction method for a spectral reflectance, comprising:

obtaining a photosynthetically active irradiance measured by a photosynthetically active radiation sensor, wherein the photosynthetically active radiation sensor comprises a cosine corrector;

obtaining a photosynthetically active irradiance of a target band based on a proportional relationship between the photosynthetically active irradiance and a downwelling solar irradiance within a same wavelength range, wherein the downwelling solar irradiance is obtained based on a standard solar spectral irradiance model, the target band is any band in a spectral band obtained by an imaging hyperspectral sensor, and an imaging time point of the imaging hyperspectral sensor is synchronized with a measurement time point of the photosynthetically active radiation sensor; and wherein the step of obtaining the photosynthetically active irradiance of the target band based on the proportional relationship between the photosynthetically active irradiance and the downwelling solar irradiance within the same wavelength range comprises:

calculating a first total value of the photosynthetically active irradiance and a second total value of the downwelling solar irradiance within the same wavelength range;

calculating a ratio of the first total value to the second total value; and calculating a product of the ratio and downwelling solar irradiance of the target band to obtain the photosynthetically active irradiance of the target band;

performing a weighted adjustment on the photosynthetically active irradiance of the target band to obtain a corrected target irradiance of the target band;

wherein the step of performing the weighted adjustment on the photosynthetically active irradiance of the target band to obtain the corrected target irradiance of the target band comprises:

within a wavelength range of the imaging hyperspectral sensor, performing the weighted adjustment on the photosynthetically active irradiance of the target band by using a spectral response function of the imaging hyperspectral sensor, to obtain the corrected target irradiance of the target band.

2. The real-time radiometric correction method for the spectral reflectance according to claim 1, after obtaining the corrected target irradiance of the target band, comprising:

calibrating a radiance of the imaging hyperspectral sensor in the target band to obtain a target radiance of the target band; and obtaining a spectral reflectance of the target band based on the corrected target irradiance and the target radiance.

3. The real-time radiometric correction method for the spectral reflectance according to claim 2, wherein the step of calibrating the radiance of the imaging hyperspectral sensor in the target band to obtain the target radiance of the target band comprises:

calibrating a radiance based on a digital number and a radiometric calibration coefficient of the imaging hyperspectral sensor in the target band to obtain the target radiance of the target band.

4. The real-time radiometric correction method for the spectral reflectance according to claim 2, wherein the step of obtaining the spectral reflectance of the target band based on the corrected target irradiance and the target radiance comprises:

obtaining the spectral reflectance of the target band based on a ratio of the target radiance to the corrected target irradiance.

5. An electronic device, comprising a processor and a memory storing a computer program, wherein the processor executes the computer program to perform steps of the real-time radiometric correction method for the spectral reflectance according to claim 1.

6. The electronic device according to claim 5, wherein in the real-time radiometric correction method for the spectral reflectance, after obtaining the corrected target irradiance of the target band, comprising:

calibrating a radiance of the imaging hyperspectral sensor in the target band to obtain a target radiance of the target band; and obtaining a spectral reflectance of the target band based on the corrected target irradiance and the target radiance.

7. The electronic device according to claim 6, wherein in the real-time radiometric correction method for the spectral reflectance, the step of calibrating the radiance of the imaging hyperspectral sensor in the target band to obtain the target radiance of the target band comprises:

calibrating a radiance based on a digital number and a radiometric calibration coefficient of the imaging hyperspectral sensor in the target band to obtain the target radiance of the target band.

8. The electronic device according to claim 6, wherein in the real-time radiometric correction method for the spectral reflectance, the step of obtaining the spectral reflectance of the target band based on the corrected target irradiance and the target radiance comprises:

obtaining the spectral reflectance of the target band based on a ratio of the target radiance to the corrected target irradiance.

9. A computer program product, comprising a computer program, wherein the computer program is executed by a processor to perform steps of the real-time radiometric correction method for the spectral reflectance according to claim 1.

10. The computer program product according to claim 9, wherein in the real-time radiometric correction method for the spectral reflectance, after obtaining the corrected target irradiance of the target band, comprising:

calibrating a radiance of the imaging hyperspectral sensor in the target band to obtain a target radiance of the target band; and obtaining a spectral reflectance of the target band based on the corrected target irradiance and the target radiance.

11. The computer program product according to claim 10, wherein in the real-time radiometric correction method for the spectral reflectance, the step of calibrating the radiance of the imaging hyperspectral sensor in the target band to obtain the target radiance of the target band comprises:

calibrating a radiance based on a digital number and a radiometric calibration coefficient of the imaging hyperspectral sensor in the target band to obtain the target radiance of the target band.

12. The computer program product according to claim 10, wherein in the real-time radiometric correction method for the spectral reflectance, the step of obtaining the spectral reflectance of the target band based on the corrected target irradiance and the target radiance comprises:

obtaining the spectral reflectance of the target band based on a ratio of the target radiance to the corrected target irradiance.

13. A non-transitory computer-readable storage medium, storing a computer program, wherein the computer program is executed by a processor to perform steps of the real-time radiometric correction method for the spectral reflectance according to claim 1.

14. The non-transitory computer-readable storage medium according to claim 13, wherein in the real-time radiometric correction method for the spectral reflectance, after obtaining the corrected target irradiance of the target band, comprising:

calibrating a radiance of the imaging hyperspectral sensor in the target band to obtain a target radiance of the target band; and obtaining a spectral reflectance of the target band based on the corrected target irradiance and the target radiance.

15. The non-transitory computer-readable storage medium according to claim 14, wherein in the real-time radiometric correction method for the spectral reflectance, the step of calibrating the radiance of the imaging hyperspectral sensor in the target band to obtain the target radiance of the target band comprises:

calibrating a radiance based on a digital number and a radiometric calibration coefficient of the imaging hyperspectral sensor in the target band to obtain the target radiance of the target band.

16. A real-time radiometric correction apparatus for a spectral reflectance, comprising:

a photosynthetically active irradiance obtaining module configured to obtain a photosynthetically active irradiance measured by a photosynthetically active radiation sensor, wherein the photosynthetically active radiation sensor comprises a cosine corrector;

a photosynthetically active irradiance calculation module configured to obtain a photosynthetically active irradiance of a target band based on a proportional relationship between the photosynthetically active irradiance and a downwelling solar irradiance within a same wavelength range, wherein the downwelling solar irradiance is obtained based on a standard solar spectral irradiance model, the target band is any band in a spectral band obtained by an imaging hyperspectral sensor, and an imaging time point of the imaging hyperspectral sensor is synchronized with a measurement time point of the photosynthetically active radiation sensor; and wherein the photosynthetically active irradiance calculation module obtains the photosynthetically active irradiance of the target band based on the proportional relationship between the photosynthetically active irradiance and the downwelling solar irradiance within the same wavelength range by:

calculating a first total value of the photosynthetically active irradiance and a second total value of the downwelling solar irradiance within the same wavelength range;

calculating a ratio of the first total value to the second total value; and calculating a product of the ratio and downwelling solar irradiance of the target band to obtain the photosynthetically active irradiance of the target band;

a photosynthetically active irradiance adjustment module configured to perform a weighted adjustment on the photosynthetically active irradiance of the target band to obtain a corrected target irradiance of the target band;

wherein the step of performing the weighted adjustment on the photosynthetically active irradiance of the target band to obtain the corrected target irradiance of the target band comprises:

within a wavelength range of the imaging hyperspectral sensor, performing the weighted adjustment on the photosynthetically active irradiance of the target band by using a spectral response function of the imaging hyperspectral sensor, to obtain the corrected target irradiance of the target band.

* * * * *